US00PP10019P

United States Patent [19]

Lemon

[11] Patent Number: Plant 10,019

[45] Date of Patent: Sep. 2, 1997

[54] GERANIUM PLANT NAMED 'SANDRA'

[75] Inventor: David Lemon, Lompoc, Calif.

[73] Assignee: John Bodger and Sons Company, South El Monte, Calif.

[21] Appl. No.: 571,164

[22] Filed: Dec. 12, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,091 1/1993 Walters ..... Plt./87.12
P.P. 8,909 9/1994 Walters ..... Plt./87.12

*Primary Examiner*—Howard J. Locker
*Attorney, Agent, or Firm*—Fulwider Patton Lee & Utecht, LLP

[57] ABSTRACT

The cultivar is characterized by its rich pink bi-color. Its compact, controlled growth habit and prolific blooms provide for superb cuttings and performs equally well in hanging baskets or as a pot plant.

1 Drawing Sheet

BACKGROUND OF THE NEW PLANT

The present invention comprises a new and distinct cultivar of *Pelargonium×domesticum* known by the varietal name Sandra (Oglevee No. 546, Bodger No. 6PD 13-4). The new variety was discovered in a selective breeding program by David Lemon at Bodger Seeds, Ltd., Lompoc, Calif. The new variety is a selection from the self-pollenation of Elsie Hickman (unpatented). Sandra was the single plant selection number 4 taken from an F2 population grown from the self-seed of Elsie Hickman.

The new cultivar was first asexually reproduced by cuttings at Oglevee Ltd., Connellsville, Pa., and has been asexually reproduced by cuttings at Oglevee Ltd. in Connellsville, Pa. It has been found to retain its distinctive characteristics through successive propagations.

The new cultivar, when grown in a glass greenhouse in Connellsville, Pa. using full light 60° Fahrenheit night temperature, 68° Fahrenheit day temperature, 72° Fahrenheit vent temperature and grown in a soilless media of constant fertilizer 150 to 200 parts per million of nitrogen and potassium has a response time of fourteen (14) weeks from the rooted cutting to a flowering plant in a 15.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Nov. 3, 1993 and flowered Feb. 10, 1994 under full light and greenhouse, and colorings were taken indoors under 200–220 foot candles of fluorescent cool white light using the R.H.S. Colour Chart of The Royal Horticultural Society of London.

THE PLANT

Classification:
*Botanical—Pelargonium×domesticum.*

Form: Upright, mound habit.
*Height.*—20.0 cm from the media surface.
*Growth.*—Compact; free branching; small leaves.
*Strength.*—Free standing; artificial support not needed; rooting ease.

Foliage: Stalked leaf attachment.

Leaves:
*Size.*—7.0–9.0 cm across.
*Shape.*—Truncate base; depressed ovate.
*Margin.*—Serratedly lobed.
*Texture.*—Leathery, slightly reflective.
*Color.* Top: Green Group 137D; Zone: Not Present; Bottom: Yellow/green Group 147B.
*Ribs and veins.*—Palmate venation: Color: Yellow/Green Group 147D.

Petioles:
*Length.*—3.0–6.0 cm.
*Color.*—Yellow/green group 146D.

Stem:
*Color.*—Yellow/green group 146D.
*Internodes.*—1.0–3.0 cm in length.

THE BUD

Shape: Elliptical.
Size: 1.5–1.75 cm across when showing faintest tint of color.

INFLORESCENCE

Blooming habit: Many large florets opening into a full flower.
Size: 10.0–12.0 cm across fully opened bloom.
Borne: Floret on pedicel; pedicel on peduncle; 8.0–10.0 cm above foliage; umbel.

Florets:
*Form.*—Cupped; semi-double.
*Color.*—Top: Upper petal marking is large, center blotch and veining Red-Purple Group 61B, peripheral marking is Red Group 52B, with petal margin Red Group 55D; other petals are similar but marking less pronounced and smaller in size. Bottom: Blotch Red-Purple Group 59A, with veining of Red-Purple Group 57 A to Red Group 55 A; balance of petal Red Group 56B fading to 56D.
Florets may generally be described as bi-colored with a light pink base and a dark scarlet red overlay. The dark scarlet red overlay is relatively large on the top two petals, and relatively small on the rest of the petals.

*Petals.*—5–7 in number; single, not united; slightly unruffled.

*Size.*—5.5–6.0 cm across.

*Texture and appearance.*—Smooth and satiny. Appearance from a distance is rich pink bi-color flower above medium green foliage.

Petaloids:

*Quantity.*—None.

Pedicel:

*Length.*—2.0–3.0 cm.

*Color.*—Yellow/green group 146D.

Peduncle:

*Length.*—6.0–cm in length.

*Color.*—Yellow/green group 146D.

Persistence:

*Disease resistance.*—Not known.

*Lasting quality.*—Blooms will last 21–25 days in a home environment.

REPRODUCTIVE ORGANS

Stamens:

*Anthers.*—2.5–5.0 mm in length.

*Filaments.*—7.5–10.0 mm in length; white slightly curved, 8–10 in number.

*Pollen.*—Golden Brown in color.

Pistils:

*Number.*—One.

*Length.*—2.0 cm.

*Stigma.*—One; 5–6 parted, purple in color.

*Style.*—1.0 cm.

Ovaries: Light green in color, 5.0–6.0 mm in length.

Fruit: None observed.

GENERAL CHARACTERISTICS

This new geranium variety, Sandra, adds a new color to the regal geranium market with a dark pink and pink bi-color bloom. The plant is very controlled in a neat mound habit.

For production purposes, Sandra is a very good cutting producer and is very easy to root. Sandra has a very long post harvest life holding bloom 8–10 weeks after the first flush of color in the greenhouse.

I claim:

1. A new and distinct variety of geranium plant, substantially as shown and described.

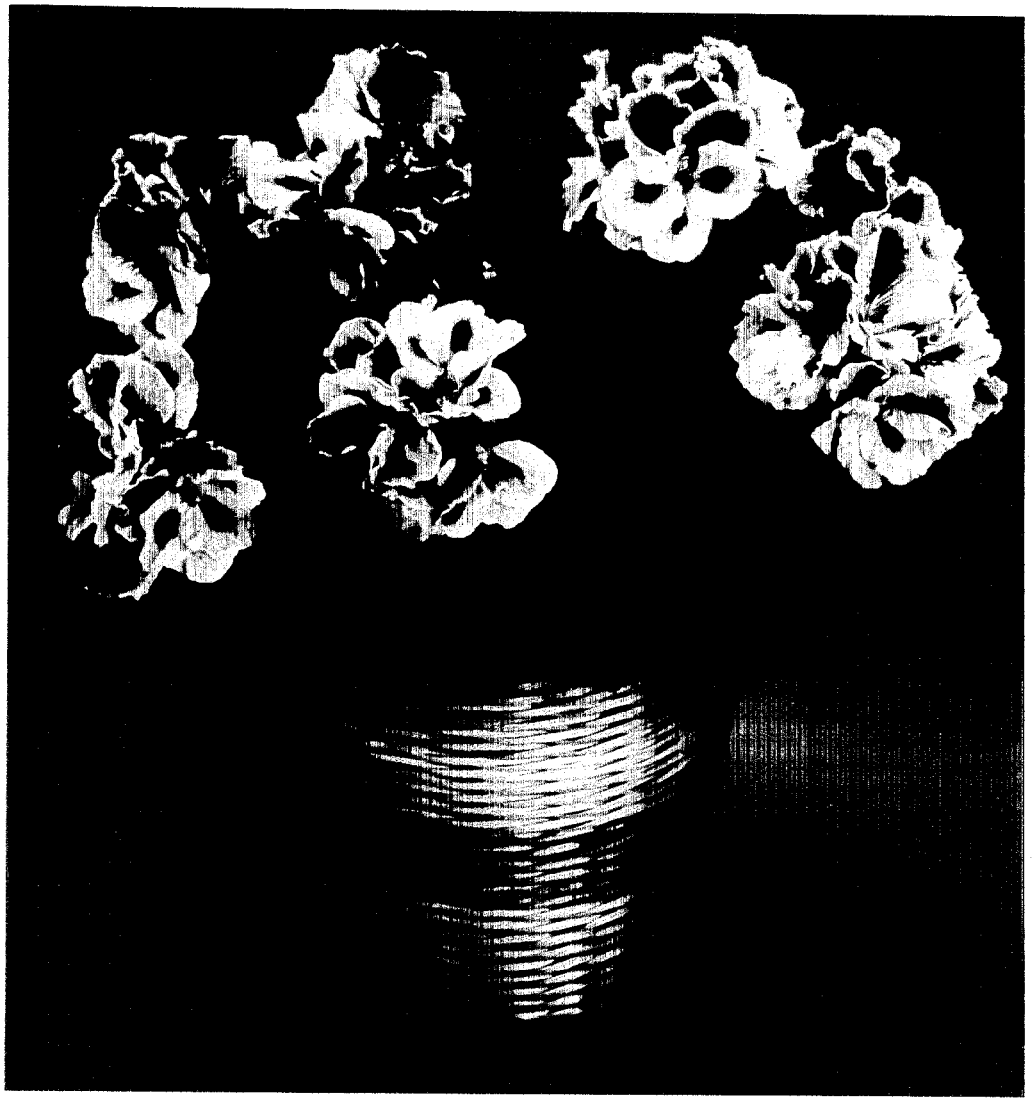

* * * * *